United States Patent [19]
Cozzi et al.

[11] Patent Number: 6,153,642
[45] Date of Patent: Nov. 28, 2000

[54] BENZOHETEROCYCLIC DISTAMYCIN DERIVATIVES, PROCESS FOR PREPARING THEM, AND THEIR USE AS ANTITUMOR AND ANTIVIRAL AGENTS

[75] Inventors: Paolo Cozzi, Milan; Pier Giovanni Baraldi, Ferrara; Italo Beria, Villamarzana; Marina Caldarelli; Laura Capolongo, both of Milan; Giampiero Spalluto; Romeo Romagnoli, both of Ferrara, all of Italy

[73] Assignee: Pharmacia & Upjohn S.p.A., Milan, Italy

[21] Appl. No.: 09/284,958

[22] PCT Filed: Oct. 23, 1997

[86] PCT No.: PCT/EP97/05986

§ 371 Date: May 4, 1999

§ 102(e) Date: May 4, 1999

[87] PCT Pub. No.: WO98/21202

PCT Pub. Date: May 22, 1998

[30] Foreign Application Priority Data

Nov. 11, 1996 [GB] United Kingdom ............... 9623522

[51] Int. Cl.⁷ ............ A61K 31/41; A61K 31/4184; C07D 403/14; C07D 407/14; C07D 409/14
[52] U.S. Cl. ............ 514/414; 548/178; 548/306.1; 548/523; 548/467; 514/367; 514/394; 514/422
[58] Field of Search ............ 548/467; 514/414

[56] References Cited

FOREIGN PATENT DOCUMENTS

| | | |
|---|---|---|
| 0 246 868 | 11/1987 | European Pat. Off. |
| 93 13739 | 7/1993 | WIPO |
| 94 20463 | 9/1994 | WIPO |
| 96 05196 | 2/1996 | WIPO |
| 97 03957 | 2/1997 | WIPO |

OTHER PUBLICATIONS

Arcamone F.M. et al.: "Synthesis, DNA–Binding Properties, and Antitumor Activity of Novel Distamycin Derivatives", Journal of Medicinal Chemistry, vol. 32, No. 4, (1989), pp. 774–778.

D'Alessio R., et al.: "Structure–activity relationship of novel distamycin A derivatives: Synthesis and antitumor activity", Bioorganic & Medicinal Chemistry Letters, vol. 4, No. 12, (Dec. 1994), pp. 1467–1472.

*Primary Examiner*—Laura L. Stockton
*Attorney, Agent, or Firm*—Arent Fox Kintner Plotkin & Kahn, PLLC

[57] ABSTRACT

Benzoheterocyclic distamycin derivatives of formula (I) wherein: n is 2, 3 or 4; A is O, S, or NR, wherein R is hydrogen or $C_1$–$C_4$ alkyl; B is CH or N; $R_1$ is hydrogen or $C_1$–$C_4$ alkyl; T is selected from; (i) formula (II) wherein: p is zero or 1; $R_2$ and $R_3$ are selected, each independently, from: hydrogen, $C_1$–$C_4$ alkyl optionally substituted by one or more fluorine atoms, and $C_1$–$C_4$ alkoxy; $R_4$ is $C_1$–$C_4$ alkyl or $C_1$–$C_3$ haloalkyl; $X_1$ is a halogen atom; and (ii) formula (III) wherein $X_2$ is a halogen atom; and pharmaceutically acceptable salts thereof, are described. Such compounds are useful as antineoplastic and antiviral agents.

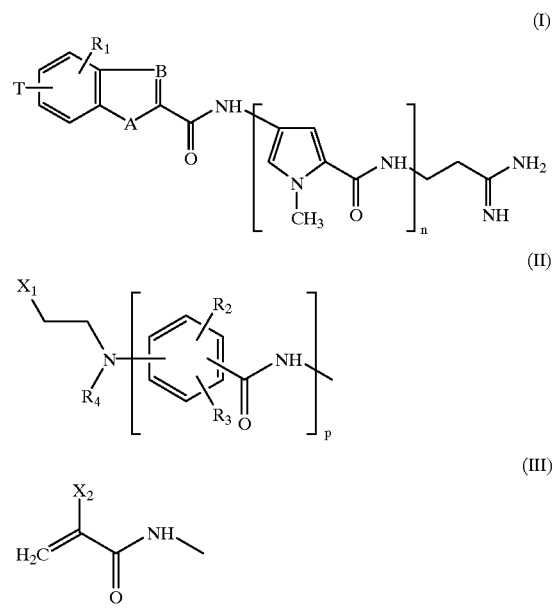

10 Claims, No Drawings

BENZOHETEROCYCLIC DISTAMYCIN DERIVATIVES, PROCESS FOR PREPARING THEM, AND THEIR USE AS ANTITUMOR AND ANTIVIRAL AGENTS

This application is a 371 of PCT/E97/05986 filed Oct. 23, 1997.

The present invention refers to new alkylating antitumor and antiviral agents related to the known antibiotic distamycin A:

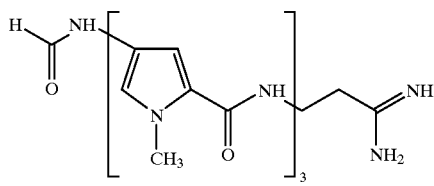

which belongs to the family of the pyrroleamidine antibiotics and is reported to interact reversibly and selectively with DNA-AT sequences interfering with both replication and transcription [Nature, 203, 1064 (1964); FEBS Letters, 7 (1970) 90; Prog.Nucleic Acids Res.Mol.Biol., 15, 285 (1975)].

DE-A-1795539 describes the preparation of distamycin derivatives in which the formyl group of distamycin is replaced by hydrogen or by the acid residue of an organic $C_1$–$C_4$ aliphatic acid or of cyclopentylpropionic acid.

EP-B-246,868 describes distamycin analogues in which the distamycin formyl group is substituted by aromatic, alicyclic or heterocyclic moieties bearing alkylating groups.

It has now been found that a new class of distamycin derivatives as defined hereinunder, wherein the distamycin formyl group is substituted by a benzoheterocyclic ring bearing an alkylating group, shows valuable biological properties.

Accordingly, the present invention relates to new distamycin derivatives of formula (I) as defined hereinunder, to a process for preparing them, to pharmaceutical compositions containing them and to their use in therapy, particularly as antitumor and antiviral agents.

Therefore, object of the present invention are distamycin derivatives of formula:

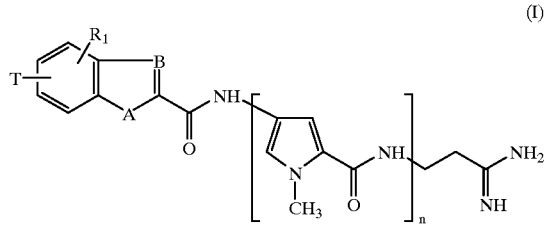

wherein:

n is 2, 3 or 4;

A is O, S or NR, wherein R is hydrogen or $C_1$–$C_4$ alkyl;

B is CH or N;

$R_1$ is hydrogen or $C_1$–$C_4$ alkyl;

T is selected from:

(i)

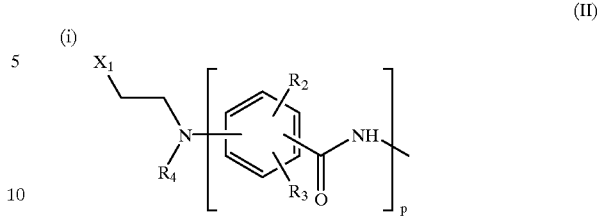

wherein:

p is zero or 1; $R_2$ and $R_3$ are selected, each independently, from: hydrogen, $C_1$–$C_4$ alkyl optionally substituted by one or more fluorine atoms, and $C_1$–$C_4$ alkoxy; $R_4$ is $C_1$–$C_4$ alkyl or $C_1$–$C_3$ haloalkyl; $X_1$ is a halogen atom; and (ii)

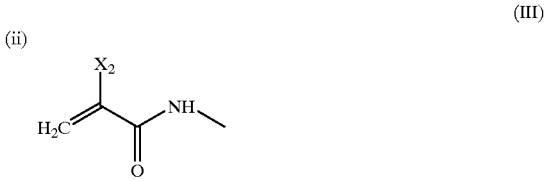

wherein $X_2$ is a halogen atom;
or pharmaceutically acceptable salts thereof.

The present invention includes within its scope also all the possible isomers covered by formula (I) both separately and in admixture, as well as the metabolites and the pharmaceutically acceptable bio-precursors (otherwise known as pro-drugs) of the compounds of formula (I).

The alkyl and alkoxy groups may have branched or straight chains. A $C_1$–$C_4$ alkyl group is preferably methyl, ethyl or propyl, a $C_1$–$C_4$ alkoxy group is preferably methoxy or ethoxy, while a $C_1$–$C_3$ haloalkyl group is preferably 2-chloroethyl or 2-bromoethyl. When substituted by one or more fluorine atoms, a $C_1$–$C_4$ alkyl group is preferably a $C_1$–$C_4$ perfluoroalkyl group, e.g. —$CF_3$. The halogen atoms $X_1$ and $X_2$ are preferably chlorine or bromine. Particularly preferred values of n are 2 and 3.

When T is an alkylating moiety of formula (II) according to item (i) above with p equal to 1, the carboxamido group and the amino group on the phenyl ring are preferably in meta or para position with respect to each other, while $R_2$ and $R_3$ can be in any of the free positions.

Pharmaceutically acceptable salts of the compounds of formula (I) are their salts with pharmaceutically acceptable, either inorganic or organic, acids. Examples of inorganic acids are hydrochloric, hydrobromic, sulfuric and nitric acid; examples of organic acids are acetic, propionic, succinic, malonic, citric, tartaric, methanesulfonic and p-toluenesulfonic acid.

A preferred class of distamycin derivatives according to the present invention is the one of formula (I) wherein:

n is 2 or 3;

A is O, S, NH or $NCH_3$;

B is CH or N;

$R_1$ is hydrogen;

T is a group of formula (II) according to item (i), wherein $X_1$ is chlorine or bromine; $R_4$ is ethyl, 2-chloroethyl or 2-bromoethyl; $R_2$ and $R_3$ are, each independently, hydrogen or methyl; p is zero or 1; or T is a group of formula (III) according to item (ii), wherein $X_2$ is bromine or chlorine.

Examples of specific compounds according to the present invention, especially in the form of salts, preferably with hydrochloric acid, are the following:

1) 3-[1-methyl-4[1-methyl-4[1-methyl-4[5-N,N-bis(2-chloroethyl)aminoindole-2-carboxamido]pyrrole-2-carboxamido]pyrrole-2-carboxamido]pyrrole-2-carboxamido]propionamidine;
2) 3-[1-methyl-4[1-methyl-4[1-methyl-4[1-methyl-5-N,N-bis(2-chloroethyl)aminoindole-2-carboxamido]pyrrole-2-carboxamido]pyrrole-2-carboxamido]pyrrole-2-carboxamido]propionamidine;
3) 3-[1-methyl-4[1-methyl-4[1-methyl-4[5-N,N-bis(2-chloroethyl)aminobenzofurane-2-carboxamido]pyrrole-2-carboxamido]pyrrole-2-carboxamido]pyrrole-2-carboxamido]propionamidine;
4) 3-[1-methyl-4[1-methyl-4[1-methyl-4[5-N,N-bis(2-chloroethyl)aminobenzoimidazole-2-carboxamido]pyrrole-2-carboxamido]pyrrole-2-carboxamido]pyrrole-2-carboxamido]propionamidine;
5) 3-[1-methyl-4[1-methyl-4[1-methyl-4[1-methyl-5-N,N-bis(2-chloroethyl)aminobenzoimidazole-2-carboxamido]pyrrole-2-carboxamido]pyrrole-2-carboxamido]pyrrole-2-carboxamido]propionamidine;
6) 3-[1-methyl-4[1-methyl-4[1-methyl-4[5-N,N-bis(2-chloroethyl)aminobenzothiophene-2-carboxamido]pyrrole-2-carboxamido]pyrrole-2-carboxamido]pyrrole-2-carboxamido]propionamidine;
7) 3-[1-methyl-4[1-methyl-4[1-methyl-4[5-N,N-bis(2-chloroethyl)aminobenzothiazole-2-carboxamido]pyrrole-2-carboxamido]pyrrole-2-carboxamido]pyrrole-2-carboxamido]propionamidine;
8) 3-[1-methyl-4[1-methyl-4[1-methyl-4[5-N,N-bis(2-bromoethyl)aminoindole-2-carboxamido]pyrrole-2-carboxamido]pyrrole-2-carboxamido]pyrrole-2-carboxamido]propionamidine;
9) 3-[1-methyl-4[1-methyl-4[1-methyl-5(α-bromoacrylamido)indole-2-carboxamido]pyrrole-2-carboxamido]pyrrole-2-carboxamido]propionamidine;
10) 3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propionamidine;
11) 3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamidine;
12) 3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propionamidine;
13) 3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propionamidine;
14) 3-[1-methyl-4[1-methyl-4[1-methyl-4[5(α-bromoacrylamido)benzothiazole-2-carboxamido]pyrrole-2-carboxamido]pyrrole-2-carboxamido]pyrrole-2-carboxamido]propionamidine;
15) 3-[1-methyl-4[1-methyl-4[1-methyl-4[5(α-bromoacrylamido)benzoimidazole-2-carboxamido]pyrrole-2-carboxamido]pyrrole-2-carboxamido]pyrrole-2-carboxamido]propionamidine;
16) 3-[1-methyl-4[1-methyl-4[1-methyl-4[1-methyl-5(α-bromoacrylamido)benzoimidazole-2-carboxamido]pyrrole-2-carboxamido]pyrrole-2-carboxamido]pyrrole-2-carboxamido]propionamidine;
17) 3-[1-methyl-4[1-methyl-4[1-methyl-4[5(αchloroacrylamido)indole-2-carboxamido]pyrrole-2-carboxamido]pyrrole-2-carboxamido]pyrrole-2-carboxamido]propionamidine;
18) 3-[1-methyl-4[1-methyl-4[1-methyl-4[1-methyl-5(α-chloroacrylamido)indole-2-carboxamido]pyrrole-2-carboxamido]pyrrole-2-carboxamido]pyrrole-2-carboxamido]propionamidine;
19) 3-[1-methyl-4[1-methyl-4[1-methyl-4[5(α-chloroacrylamido)benzoimidazole-2-carboxamido]pyrrole-2-carboxamido]pyrrole-2-carboxamido]pyrrole-2-carboxamido]propionamidine;
20) 3-[1-methyl-4[1-methyl-4[5-[4-N,N-bis(2-chloroethyl)aminobenzene-1-carboxamido]indole-2-carboxamido]pyrrole-2-carboxamido]pyrrole-2-carboxamido]propionamidine;
21) 3-[1-methyl-4[1-methyl-4[5-[4-N,N-bis(2-chloroethyl)aminobenzene-1-carboxamido]benzoimidazole-2-carboxamido]pyrrole-2-carboxamido]pyrrole-2-carboxamido]propionamidine;
22) 3-[1-methyl-4[1-methyl-4[1-methyl-4[5-[4-N,N-bis(2-chloroethyl)aminobenzene-1-carboxamido]indole-2-carboxamido]pyrrole-2-carboxamido]pyrrole-2-carboxamido]pyrrole-2-carboxamido]propionamidine;
23) 3-[1-methyl-4[1-methyl-4[1-methyl-4[1-methyl-5-[4-N,N-bis(2-chloroethyl)aminobenzene-1-carboxamido]indole-2-carboxamido]pyrrole-2-carboxamido]pyrrole-2-carboxamido]pyrrole-2-carboxamido]propionamidine;
24) 3-[1-methyl-4[1-methyl-4[1-methyl4[5-[4-N,N-bis(2-chloroethyl)aminobenzene-1-carboxamido]benzothiophene-2-carboxamido]pyrrole-2-carboxamido]pyrrole-2-carboxamido]pyrrole-2-carboxamido]propionamidine;
25) 3-[1-methyl-4[1-methyl-4[1-methyl4[5-[4-N,N-bis(2-chloroethyl)aminobenzene-1-carboxamido]benzofurane-2-carboxamido]pyrrole-2-carboxamido]pyrrole-2-carboxamido]pyrrole-2-carboxamido]propionamidine;
26) 3-[1-methyl-4[1-methyl-4[1-methyl-4[5-[4-N,N-bis(2-chloroethyl)aminobenzene-1-carboxamido]benzoimidazole-2-carboxamido]pyrrole-2-carboxamido]pyrrole-2-carboxamido]pyrrole-2-carboxamido]propionamidine;
27) 3-[1-methyl-4[1-methyl-4[1-methyl-4[1-methyl-5-[4-N,N-bis(2-chloroethyl)aminobenzene-1-carboxamido]benzoimidazole-2-carboxamido]pyrrole-2-carboxamido]pyrrole-2-carboxamido]pyrrole-2-carboxamido]propionamidine;
28) 3-[1-methyl-4[1-methyl-4[1-methyl-4[5-[4-N,N-bis(2-chloroethyl)aminobenzene-1-carboxamido]benzothiazole-2-carboxamido]pyrrole-2-carboxamido]pyrrole-2-carboxamido]pyrrole-2-carboxamido]propionamidine;
29) 3-[1-methyl-4[1-methyl-4[5-[4-N,N-bis(2-bromoethyl)aminobenzene-1-carboxamido]indole-2-carboxamido]pyrrole-2-carboxamido]pyrrole-2-carboxamido]propionamidine;
30) 3-[1-methyl-4[1-methyl-4[1-methyl-5-[4-N,N-bis(2-bromoethyl)aminobenzene-1-carboxamido]indole-2-carboxamido]pyrrole-2-carboxamido]pyrrole-2-carboxamido]propionamidine;
31) 3-[1-methyl-4[1-methyl-4[5-[4-N,N-bis(2-bromoethyl)aminobenzene-1-carboxamido]benzoimidazole-2-carboxamido]pyrrole-2-carboxamido]pyrrole-2-carboxamido]propionamidine;
32) 3-[1-methyl-4[1-methyl-4[1-methyl-4[5-[4-N,N-bis(2-bromoethyl)aminobenzene-1-carboxamido]indole-2-carboxamido]pyrrole-2-carboxamido]pyrrole-2-carboxamido]pyrrole-2-carboxamido]propionamidine;

33) 3-[1-methyl-4[1-methyl-4[1-methyl-4[1-methyl-5-[4-N,N-bis(2-bromoethyl)aminobenzene-1-carboxamido]indole-2-carboxamido]pyrrole-2-carboxamido]pyrrole-2-carboxamido]pyrrole-2-carboxamido]propionamidine;

34) 3-[1-methyl-4[1-methyl-4[1-methyl-4[5-[4-N,N-bis(2-bromoethyl)aminobenzene-1-carboxamido]benzoimidazole-2-carboxamido]pyrrole-2-carboxamido]pyrrole-2-carboxamido]pyrrole-2-carboxamido]propionamidine;

35) 3-[1-methyl-4[1-methyl-4[1-methyl-4[5-[4-N-ethyl-N(2-chloroethyl)aminobenzene-1-carboxamido]indole-2-carboxamido]pyrrole-2-carboxamido]pyrrole-2-carboxamido]pyrrole-2-carboxamido]propionamidine;

36) 3-[1-methyl-4[1-methyl-4[1-methyl-4[5-[4-N-ethyl-N(2-chloroethyl)aminobenzene-1-carboxamido]benzoimidazole-2-carboxamido]pyrrole-2-carboxamido]pyrrole-2-carboxamido]pyrrole-2-carboxamido]propionamidine;

37) 3-[1-methyl-4[1-methyl-4[1-methyl-4[1-methyl-5-[4-N-ethyl-N(2-chloroethyl)aminobenzene-1-carboxamido]indole-2-carboxamido]pyrrole-2-carboxamido]pyrrole-2-carboxamido]pyrrole-2-carboxamido]propionamidine;

38) 3-[1-methyl-4[1-methyl-4[1-methyl-4[1-methyl-5-[-4-N-ethyl-N(2-chloroethyl)aminobenzene-1-carboxamido]benzoimidazole-2-carboxamido]pyrrole-2-carboxamido]pyrrole-2-carboxamido]pyrrole-2-carboxamido]propionamidine.

Further object of the present invention is a process for preparing the compounds of formula (I), and the pharmaceutically acceptable salts thereof, which comprises:

(1)(a) reacting a compound of formula:

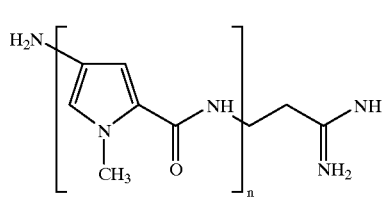
(IV)

wherein n is 2, 3 or 4, with a compound of formula:

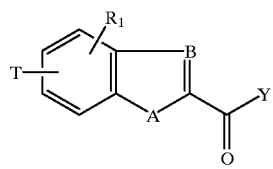
(V)

wherein:
A is O, S or NR, wherein R is hydrogen or $C_1$–$C_4$ alkyl;
B is CH or N;
$R_1$ is hydrogen or $C_1$–$C_4$ alkyl;

T is selected from:

(i)

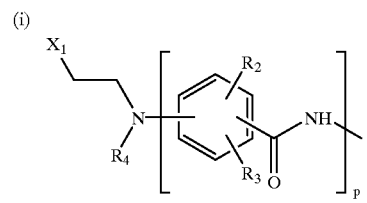
(II)

wherein:
p is zero or 1; $R_2$ and $R_3$ are selected, each independently, from: hydrogen, $C_1$–$C_4$ alkyl optionally substituted by one or more fluorine atoms, and $C_1$–$C_4$ alkoxy; $R_4$ is $C_1$–$C_4$ alkyl or $C_1$–$C_3$ haloalkyl; $X_1$ is a halogen atom; and (ii)

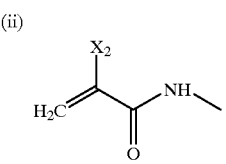
(III)

wherein
$X_2$ is a halogen atom;
Y is hydroxy or a leaving group;

to obtain a compound of formula (I) as defined above; or:

(b) reacting a compound of formula:

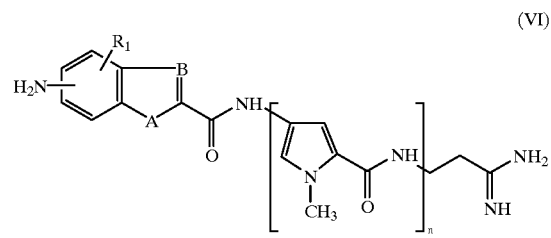
(VI)

wherein n, A, B, and $R_1$ are defined as above, with a compound of formula:

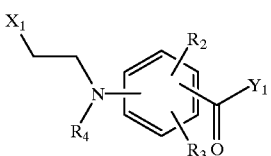
(VIIa)

wherein $X_1$, $R_2$, $R_3$, and $R_4$ are defined as above, and $Y_1$ is hydroxy or a leaving group;

or with a compound of formula:

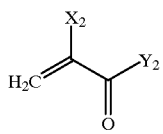

(VIIb)

wherein $X_2$ is as defined above, and $Y_2$ is hydroxy or a leaving group;
to obtain a compound of formula (I) as defined above, wherein T is a group of formula (II) according to item (i) with p equal to 1, or a group of formula (III) according to item (ii); or:
(c) reacting a compound of formula:

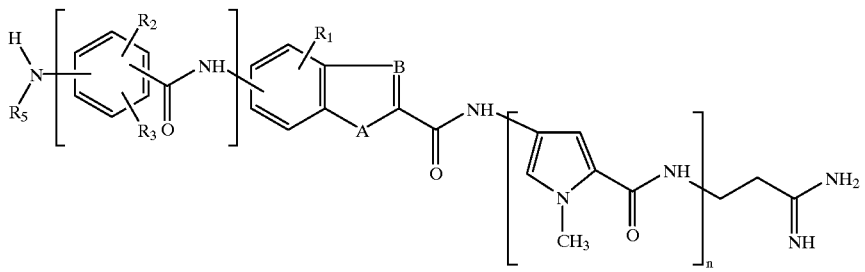

(VIII)

wherein p, n, A, B, $R_1$, $R_2$, and $R_3$ are defined as above and $R_5$ is hydrogen or $C_1$–$C_4$ alkyl, with ethylene oxide, so obtaining a compound of formula:

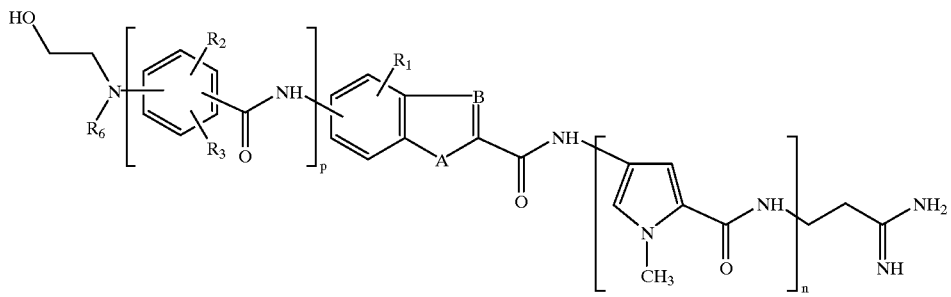

(IX)

wherein p, n, A, B, $R_1$, $R_2$, and $R_3$ are defined as above, and $R_6$ is equal to $R_5$ when $R_5$ is $C_1$–$C_4$ alkyl, or $R_6$ is equal to —$CH_2CH_2$—OH when $R_5$ is hydrogen;
and then reacting the compound of formula (IX) with a halogenating agent, to obtain a compound of formula (I) as defined above, wherein T is a group of formula (II) according to item (i) with p equal to zero or 1; and
(2) if necessary, converting the so obtained compound of formula (I) into a pharmaceutically acceptable salt thereof.

The reaction of a compound of formula (IV) with a compound of formula (V) (process (a)) can be carried out according to known methods, for instance those described in EP-B-246,868.

The reaction between a compound of formula (IV) and a compound of formula (V) wherein Y is hydroxy, is prefer- ably carried out with a molar ratio (IV):(V) of from 1:1 to 1:2, in an organic solvent, such as, e.g., dimethylsulphoxide, dimethylacetamide, dimethylformamide, ethanol, benzene, or pyridine, in the presence of an organic or inorganic base such as, e.g., triethylamine, N,N'-diisopropylethylamine, or sodium or potassium carbonate or bicarbonate, and a con- densing agent such as, e.g., N-ethyl-N'-(3-dimethylaminopropyl)carbodiimide, N,N'-dicyclohexylcarbodiimide, or 1-hydroxybenzotriazole hydrate. The reaction temperature may vary from about –10° C. to about 100° C., and the reaction time from about 1 to about 24 hours.

The reaction between a compound of formula (IV) and a compound of formula (V), wherein Y is a leaving group as defined above, may be carried out with a molar ratio (IV) (V) of from about 1:1 to about 1:2, in an organic solvent, such as, e.g., dimethylformamide, dioxane, pyridine, tetrahydrofurane, or mixtures thereof with water, optionally in the presence of an organic base, e.g. N,N'-diisopropylethylamine, triethylamine, or an inorganic base, e.g. sodium or potassium bicarbonate, at a temperature of from about 0° C. to about 100° C., and for a time varying from about 2 hours to about 48 hours.

The compounds of formula (IV) are known compounds, or may be prepared by known methods from known com- pounds: see, for instance, Arcamone et al. Gazzetta Chim. Ital. 97, 1097 (1967).

The compounds of formula (V), wherein Y is hydroxy, and T is a group of formula (II) according to item (i) with p equal to 1, or a group of formula (III) according to item (ii), can be prepared by reacting an amino compound of formula:

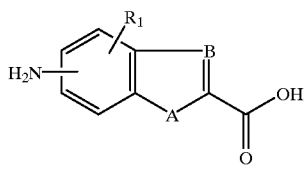
(X)

wherein A, B and $R_1$ are as defined above, with a carboxylic acid, or a derivative thereof, of formula (VIIa) or (VIIb) as defined above.

The compounds of formula (V), wherein Y is hydroxy, and T is a group of formula (II) according to item (i) with p equal to zero, can be prepared by reacting a compound of formula:

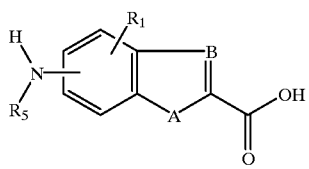
(XI)

wherein A, B, $R_1$, and $R_5$ are defined as above, with ethylene oxide and then with a halogenating agent, analogously to what described above for process (c). Before carrying out the reaction, the carboxyl group is preferably protected with a suitable protecting group according to known techniques.

The compounds of formula (V) wherein Y is a leaving group can be prepared starting from the corresponding acids through well known reactions.

The carboxylic acids of formulas (VIIa) and (VIIb), or the derivatives thereof, are commercially available products, or may be prepared through reactions well known in organic chemistry (see e.g. Tetrahedron Letters 31 1299 (1990), Anti-cancer Drug Design 9, 511 (1994)), JACS 62 3495 (1940), J.Org.Chem. 26 4996–97 (1961), or Synth.Commun. 24 3129–3134 (1994)).

The compounds of formulas (X) and (XI) are commercial products, or can be obtained by known methods (see e.g. J.Am.Chem.Soc. 80, 4621 (1958), Helv.Chim.Acta 31, 75 (1948), Synth.Commun. 21, 959 (1991), Anti-cancer Drug Design 10, 25 (1995), J.Org.Chem. 26, 4996–97 (1961), or Synth.Commun. 24, 3129–3134 (1994)).

The compounds of formula (VI) can be obtained by nitro-group reduction, according to known methods, of compounds of formula:

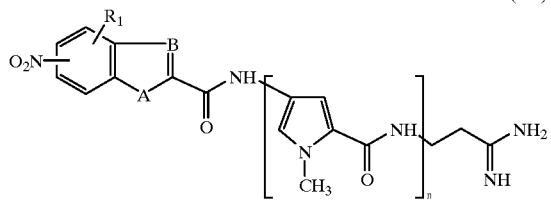
(XII)

wherein n, A, B and $R_1$ are as defined above.

The nitro-derivatives of formula (XII) can be obtained, in turn, by reacting a compound of formula (IV) as defined above with a compound of formula:

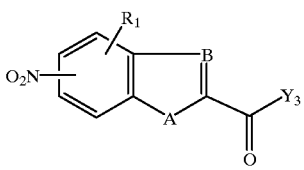
(XIII)

wherein A, B and $R_1$ are as defined above, and $Y_3$ is hydroxy or a leaving group. The compounds of formula (XIII) are known compounds, or may be obtained by known methods (see, e.g., Tetrahedron Letters 31, 1299 (1990), Anti-cancer Drug Design 9, 511 (1994)), JACS 62, 3495 (1940), J.Org.Chem. 26, 4996–97 (1963), or Synth.Commun. 24, 3129–3134 (1994)).

The reaction according to process (c) can be carried out analogously to what described in U.S. Pat. No. 4,738,980. The halogenating agent may be, e.g., an elemental halide, such as chlorine or bromine, or a thionyl halide, such as thionylchloride. The starting compounds of formula (VIII) may be obtained according to know reactions, e.g. by mono-alkylation of the amino-compounds of formula (VI) as defined above, optionally previously condensed with the corresponding amino benzoic acid, or a derivative thereof.

In the above formulas, the groups Y, $Y_1$, $Y_2$, and $Y_3$ are hydroxy or leaving groups selected, for instance, from chloro, 2,4,5-trichlorophenoxy, 2,4-dinitro-phenoxy, succinimido-N-oxy, imidazolyl, and the like.

Salification of a compound of formula (I), as well as preparation of a free compound starting from a salt, may be carried out by known standard methods. Well known procedures such as, e.g., fractional crystallization or chromatography, may also be followed for separating a mixture of isomers of formula (I) into the single isomers.

The compounds of formula (I) may be purified by conventional techniques such as, e.g., silica gel or alumina column chromatography, and/or by recrystallization from an organic solvent such as, e.g., a lower aliphatic alcohol, e.g. methyl, ethyl or isopropyl alcohol, or dimethylformamide.

Pharmacology

The compounds of formula (I) according to the present invention are useful as antineoplastic and antiviral agents. Particularly, they show cytostatic properties towards tumor cells, so that they can be useful to inhibit growth of various tumors in mammals, including humans, such as, for instance, carcinomas, e.g. mammary carcinoma, lung carcinoma, bladder carcinoma, colon carcinoma, ovary and endometrial tumors. Other neoplasias in which the compounds of the present invention can find application are, for instance, sarcomas, e.g. soft tissue and bone sarcomas, and the hematological malignancies such as, e.g. leukemias.

The in vitro antitumor activity was evaluated by cytotoxicity studies carried out on murine $L_{1210}$ leukemia cells. Cells were derived from in vivo tumors and established in cell culture. Cells were used until the tenth passage. Cytotoxicity was determined by counting surviving cells after 48 hours treatment.

The percentage of cell growth in the treated cultures was compared with that of controls. $IC_{50}$ values (concentration inhibiting 50% of the cellular growth in respect to controls) were calculated on dose-response.

The compounds of the invention were tested also in vivo on $L_{1210}$ murine leukemia and on murine reticulosarcoma M 5076, showing a very good antitumoral activity, with the following procedure.

$L_{1210}$ murine leukemia was maintained in vivo by i.v. serial transplantation. For experiments, $10^5$ cells were injected i.p. in CD2F1 female mice, obtained from Charles River Italy. Animals were 8 to 10 weeks old at the beginning of the experiments. Compounds were administered i.v. at day +1 after tumor cells injections.

M5076 reticulosarcoma was maintained in vivo by i.m. serial transplantation. For experiments, $5 \times 10^5$ cells were injected i.m. in C57B16 female mice, obtained from Charles River Italy. Animals were 8 to 10 weeks old at the beginning of the experiments. Compounds were administered i.v. at day 3, 7 and 11 after tumor injection.

Survival time of mice and tumor growth were calculated and activity was expressed in terms of T/C % and T.I. %.

$$T/C = \frac{\text{median survival time treated group}}{\text{median survival time untreated group}} \times 100$$

T.I.=% inhibition of tumor growth respect to control

Tox=number of mice which died for toxicity.

Tox determination was made when mice died before the control and/or tested significant body weight loss and/or spleen and/or liver size reduction were observed.

The compounds of the invention show also a remarkable effectiveness in interfering with the reproductive activity of pathogenic viruses and protect tissue cells from viral infections. For example, they show activity against DNA viruses such as, for instance, herpes, e.g. herpes simplex and herpes zoster viruses, virus vaccinia, RNA viruses such as, e.g., Rhinovirus and Adenovirus, and against retroviruses such as, for instance, sarcoma viruses, e.g., murine sarcoma virus, and leukemia viruses, e.g. Friend leukemia virus.

For example, effectiveness against herpes, coxsackie and respiratory syncytial viruses was tested in a fluid medium as follows. Serial two-fold dilutions of the compounds from 200 to 1.5 mcg/ml were distributed in duplicate 0.1 ml/well in 96 well microplates for tissue culture. Cell suspensions ($2 \times 10^5$ cells/ml) infected with about $5 \times 10^{-3}$ TCID$_{50}$ of virus/cell were immediately added 0.1 ml/well.

After 3–5 day incubation at 37° C. in CO$_2$ 5%, the cell cultures were evaluated by microscope observation and Minimum Inhibiting Concentration (MIC) was determined, MIC being the minimum concentration which determines a reduction of cytopathic effect in comparison with the infected controls.

The compounds of the invention can be administered to mammals, including humans, through the usual routes, for example, parenterally, e.g. by intravenous injection or infusion, intramuscularly, subcutaneously, topically or orally. The dosage depends on the age, weight and conditions of the patient and on the administration route. For example, a suitable dosage for administration to adult humans may range from about 0.1 to about 150–200 mg pro dose 1–4 times a day.

Further object of the present invention are pharmaceutical compositions, which comprise a compound of formula (I) as an active principle, in association with one or more pharmaceutically acceptable carrier and/or diluent.

The pharmaceutical compositions of the present invention are usually prepared following conventional methods and are administered in a pharmaceutically suitable form. For instance, solutions for intravenous injection or infusion may contain as a carrier, for example, sterile water or preferably, they may be in the form of sterile aqueous isotonic saline solutions.

Suspensions or solutions for intramuscular injections may contain, together with the active compound a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulation. Said pharmaceutical preparation may be manufactered by known techniques, for example by means of mixing, granulating, tabletting, sugar-coating or film-coating processes.

Further object of the present invention are compounds of formula (I) for use in a method for treating the human or animal body by therapy.

Furthermore, the present invention provides a method for treating tumors and viral infections in a patient in need of it, which comprises administering to said patient a composition of the invention.

A further object of the present invention is a combined method for treating cancer or for ameliorating the conditions of mammals, including humans, suffering from cancer, said method comprising administering a compound of formula (I), or a pharmaceutically acceptable salt thereof, and an additional antitumor agent, close enough in time and in amounts sufficient to produce a therapeutically useful effect.

The present invention also provides products containing a compound of formula (I), or a pharmaceutically acceptable salt thereof, and an additional antitumour agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Examples of antitumor agents that can be formulated with a compound of formula (I), or alternatively, can be administered in a combined method of treatment, include doxorubicin, daunomycin, epirubicin, idarubicin, etoposide, fluoro-uracil, melphalan, cyclophosphamide, 4-demethoxy daunorubicin, bleomycin, vinblastin, and mitomycin, or mixtures thereof.

The following examples are given to better illustrate the invention, but do not limit the scope of the invention itself.

EXAMPLE 1

3-[1-methyl-4[1-methyl-4[1-methyl-4[5-N,N-bis(2-chloroethyl)aminoindole-2-carboxamido]pyrrole-2-carboxamido]pyrrole-2-carboxamido]pyrrole-2-carboxamido]propionamidine hydrochloride Step I: The intermediate 5-N,N-bis(2-chloroethyl) aminoindole-2-carboxylic acid To a solution of 200 mg of ethyl 5-aminoindole-2-carboxylate (prepared as reported in J.Am.Chem.Soc. 80, 4621 (1958)) in 10 ml of methanol cooled at −10° C., cold ethylene oxide (2.5 ml) was added. The reaction flask was sealed and allowed to reach room temperature overnight. Methanol and excess of ethylene oxide were removed by evaporation and the crude residue purified by flash chromatography obtaining 230 mg of ethyl 5-N,N-bis(2-hydroxyethyl)aminoindole-2-carboxylate which was cooled in ice and 2 ml of phosphorus oxychloride were added. The solution was heated at 100° C. for one hour, then solvent evaporated under vacuum, the residue dissolved in 7 ml of 23% hydrochloric acid and heated at 100° C. for two hours. The solution was cooled at room temperature, diluted with 30 ml of water and extracted twice with ethyl acetate (2×50 ml). The organic phases were evaporated in vacuo and the residue purified by flash chromatography using a methylene chloride/methanol mixture, yielding 220 mg of the intermediate.

By analogous procedure and using the opportune starting materials the following products can be obtained:

5-N,N-bis(2-chloroethyl)aminobenzofurane-2-carboxylic acid;
1-methyl-5-N,N-bis(2-chloroethyl)aminoindole-2-carboxylic acid;
5-N,N-bis(2-chloroethyl)aminobenzothiophene-2-carboxylic acid
5-N,N-bis(2-chloroethyl)aminobenzoimidazole-2-carboxylic acid;
1-methyl-5-N,N-bis(2-chloroethyl)aminobenzoimidazole-2-carboxylic acid;
5-N,N-bis(2-chloroethyl)aminobenzothiazole-2-carboxylic acid;
5-[4-N,N-bis(2-chloroethyl)aminobenzene-1-carboxamido]indole-2-carboxylic acid;
5-[4-[N-ethyl-N(2-chloroethyl)]aminobenzene-1-carboxamido]indole-2-carboxylic acid;
5-N,N-bis(2-bromoethyl)aminoindole-2-carboxylic acid;
5-[4-N,N-bis(2-bromoethyl)aminobenzene-1-carboxamido]indole-2-carboxylic acid.

Step II: The Title Compound

A solution of 263 mg of N-deformyldistamycin A dihydrochloride (prepared as reported in J.Med.Chem. 32, 774–778 (1989)) in 5 ml of dry dimethylformamide (DMF) was cooled to 5° C. and added with 86 ml of N,N'-diisopropylethylamine. After 10 min, 175 mg of intermediate obtained from step I and 192 mg of N-ethyl-N'-(3-dimethylaminopropyl)carbodiimide (EDCI) were added. The reaction was stirred at room temperature for 10 hours, then 2N hydrochloric acid was added up to pH=4. The solvent was removed under reduced pressure and the crude residue purified by flash chromatography (methylene chloride/methanol:8/2) to give 210 mg of the title compound as a yellow solid.

FAB-MS: m/z 736, (20, [M+H]$^+$)

PMR (DMSO-d$_6$) δ: 11.35 (d, J=1.8 Hz, 1H), 10.29 (s, 1H), 9.96 (s, 1H), 9.89 (s, 1H), 8.93 (b.s., 2H), 8.56 (b.s., 2H), 8.18 (t, J=5.6 Hz, 1H), 7.30 (m, 2H), 7.10 (d, J=1.8 Hz, 1H), 7.20 (d, J=1.8 Hz, 1H), 7.14 (d, J=1.8 Hz, 1H), 7.04 (d, J=1.8 Hz, 1H) 7.02 (d, J=1.8 Hz, 1H), 6.92 (d, J=1.8 Hz, 1H), 6.91 (d, J=1.8 Hz, 1H), 6.84 (dd, J=2.3 Hz and J=9.0 Hz, 1H), 3.84 (s, 3H), 3.80 (s, 3H), 3.76 (s, 3H), 3.66 (m, 8H), 3.46 (m, 2H), 2.57 (m, 2H)

By analogous procedure and using the opportune starting materials the following products can be obtained:

3-[1-methyl-4[1-methyl-4[1-methyl-4[1-methyl-5-N,N-bis(2-chloroethyl)aminoindole-2-carboxamido]pyrrole-2-carboxamido]pyrrole-2-carboxamido]pyrrole-2-carboxamido]propionamidine hydrochloride;
FAB-MS: m/z 750, (25, [M+H]$^+$)
PMR (DMSO-d$_6$) δ: 10.35 (s, 1H), 9.99 (s, 1H), 9.92 (s, 1H), 8.97 (b.s., 2H), 8.60 (b.s., 2H), 8.22 (t, J=5.5 Hz, 1H), 7.43 (d, J=9.8 Hz, 1H), 6.9–7.4 (m, 9H), 3.96 (s, 3H), 3.87 (s, 3H), 3.84 (s, 3H), 3.81 (s, 3H), 3.72 (m, 8H), 3.50 (m, 2H), 2.61 (m, 2H);

3-[1-methyl-4[1-methyl-4[1-methyl-4[5-N,N-bis(2-chloroethyl)aminobenzofurane-2-carboxamido]pyrrole-2-carboxamido]pyrrole-2-carboxamido]pyrrole-2-carboxamido]propionamidine hydrochloride;
FAB-MS: m/z 737, (20, [M+H]$^+$)
PMR (DMSO-d$_6$) δ: 10.60 (s, 1H), 9.98 (s, 1H), 9.90 (s, 1H), 8.94 (b.s., 2H) 8.56 (b.s., 2H), 8.19 (t, J=5.6 Hz, 1H), 7.52 (d, J=9.0 Hz, 1H), 7.50 (s, 1H), 6.9–7.4 (m, 8H), 3.86 (s, 3H), 3.84 (s, 3H), 3.80 (s, 3H), 3.75 (m, 8H), 3.50 (m, 2H), 2.61 (m, 2H);

3-[1-methyl-4[1-methyl-4[1-methyl-4[5-N,N-bis(2-chloroethyl)aminobenzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[1-methyl-5-N,N-bis(2-chloroethyl)aminobenzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-N,N-bis(2-chloroethyl)aminobenzothiophene-2-carboxamido]pyrrole-2-carboxamido]pyrrole-2-carboxamido]pyrrole-2-carboxamido]propionamidine hydrochloride;
FAB-MS: m/z 753, (60, [M+H]$^+$)
PMR (DMSO-d$_6$) δ: 10.55 (s, 1H), 9.97 (s, 1H), 9.89 (s, 1H), 8.17 (t, J=5.9 Hz, 1H), 8.06 (s, 1H), 7.81 (d, J=9.0 Hz, 1H), 7.29 (d, J=1.7 Hz, 1H), 7.23 (d, J=1.7 Hz, 1H), 7.21 (d, J=2.6 Hz, 1H), 7.16 (d, J=1.7 Hz, 1H), 7.09 (d, J=1.7 Hz, 1H), 7.06 (d, J=1.7 Hz, 1H), 7.06 (dd, J=9.0, 2.6 Hz, 1H), 6.95 (d, J=1.7 Hz, 1H), 3.7–3.9 (m, 8H), 3.87 (s, 3H), 3.84 (s, 3H), 3.80 (s, 3H), 3.48 (m, 2H), 2.58 (t, J=6.6 Hz, 2H);

3-[1-methyl-4[1-methyl-4[1-methyl-4[5-N,N-bis(2-chloroethyl)aminobenzothiazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-N,N-bis(2-bromoethyl)aminoindole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[1-methyl-5-[4-N,N-bis(2-chloroethyl)aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[5-[4-N,N-bis(2-bromoethyl)aminobenzene-1-carboxamido]indole-2-carboxamido]pyrrole-2-carboxamido]pyrrole-2-carboxamido]propionamidine hydrochloride;

3-[1-methyl-4[1-methyl-4[1-methyl-4[5-[4-N,N-bis(2-bromoethyl aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N-ethyl-N(2-chloroethyl)aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5(α-bromoacrylamido)benzoimidazole-2-carboxamido]pyrrole-2-carboxamido]pyrrole-2-carboxamido]pyrrole-2-carboxamido]propionamidine hydrochloride.

EXAMPLE 2

3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propionamidine hydrochloride Step I: The intermediate 5-α-bromoacrylamidobenzofurane-2-carboxylic acid To a solution of 500 mg of commercial α-bromoacrylic acid in 5 ml of acetonitrile, a solution of 343 mg of N,N-dicyclohexylcarbodiimide in 15 ml of acetonitrile was slowly added. After one hour, the solution obtained after filtration of the precipitate was added to a solution of 294 mg of 5-amino-2-benzofuranic acid (prepared as reported in Helv.Chim.Acta 31, 75 (1948)) and 229 mg of sodium bicarbonate in 20 ml of water. The reaction was stirred at room temperature for one hour, then 2N hydrochloric acid was added up to pH=4. The solution was extracted with ethyl acetate (3×10 ml), dried over sodium sulfate and evaporated to dryness in vacuo and the crude residue purified by flash chromatography with a methylene chloride/methanol mixture to yield 500 mg of the intermediate as a pale yellow solid.

By analogous procedure and using the opportune starting materials the following products can be obtained:
5-α-bromoacrylamidobenzothiophene-2-carboxylic acid;
5-α-bromoacrylamidoindole-2-carboxylic acid;
1-methyl-5-α-bromoacrylamidoindole-2-carboxylic acid;
5-α-bromoacrylamidobenzoimidazole-2-carboxylic acid;
1-methyl-5-α-bromoacrylamidobenzoimidazole-2-carboxylic acid;
5-α-bromoacrylamidobenzothiazole-2-carboxylic acid;
5-α-chloroacrylamidoindole-2-carboxylic acid;
1-methyl-5-α-chloroacrylamidoindole-2-carboxylic acid;
5-α-chloroacrylamidobenzoimidazole-2-carboxylic acid.

Step II: The Title Compound

A solution of 263 mg of N-deformyldistamycin A dihydrochloride (prepared as reported in J.Med.Chem. 32, 774–778 (1989)) in 5 ml of dry DMF was cooled to 5° C. and added with 0.086 ml of N,N'-diisopropylethylamine. After 10 min, 180 mg of the intermediate obtained from step I, and 192 mg of N-ethyl-N'-(3-dimethylaminopropyl)carbodiimide (EDCI) were added. The reaction was stirred at room temperature for 16 hours, then 2N hydrochloric acid was added up to pH=4. The solvent was evaporated in vacuo and the crude residue purified by flash chromatography (methylene chloride/methanol:8/2) to yield a yellow oil which was precipitated from methanol/diethyl ether obtaining 240 mg of the title compound as a pale yellow solid.

FAB-MS: m/z 746, (25, [M+H]$^+$)

U.V. (EtOH 95%) $\lambda_{max}$=315.4 , $\epsilon$=42622

PMR (DMSO-d$_6$) δ: 10.69 (s, 1H), 10.39 (s, 1H), 10.00 (s, 1H), 9.90 (s, 1H), 8.92 (b.s., 2H), 8.52 (b.s., 2H), 8.2 (m, 2H), 7.66 (m, 3H), 7.32 (d, J=1.8 Hz, 1H), 7.24 (d, J=1.8 Hz, 1H), 7.17 (d, J=1.8 Hz, 1H), 7.15 (d, J=1.8 Hz, 1H) 7.07 (d, J=1.8 Hz, 1H), 6.96 (d, J=1.8 Hz, 1H), 6.77 (d, J=3.1 Hz, 1H), 6.31 (d, J=3.1 Hz, 1H), 3.87 (s, 3H), 3.84 (s, 3H), 3.80 (s, 3H), 3.51 (m, 2H), 2.60 (m, 2H).

By analogous procedure and using the opportune starting materials the following products can be obtained:

3-[1-methyl-4[1-methyl-4[1-methyl-5(α-bromoacrylamido)indole-2-carboxamido]pyrrole-2-carboxamido]pyrrole-2-carboxamido]propionamidine hydrochloride;
FAB-MS: m/z 269, (10, [M+H]$^+$)
U.V. (EtOH 95%) $\lambda_{max}$=310 , $\epsilon$=35011
PMR (DMSO-d$_6$) δ: 10.39 (s, 1H), 10.18 (s, 1H), 9.93 (s, 1H), 8.92 (b.s., 2H), 8.54 (b.s., 2H), 8.19 (t, J=5.7 Hz, 1H), 8.01 (d, J=1.5 Hz, 1H), 7.50 (d, J=9 0 Hz, 1H), 7.42 (dd, J=9.0 Hz and J=1.5 Hz, 1H), 7.29 (d, J=1.8 Hz, 1H), 7.16 (d, 1H), 7.15 (d, J=1.8 Hz, 1H) 7.06 (d, J=1.8 Hz, 1H), 6.92 (d, J=1.8 Hz, 1H), 6.72 (d, J=3.1 Hz, 1H), 6.25 (d, J=3.1 Hz, 1H), 3.97 (s, 3H), 3.83 (s, 3H), 3.77 (s, 3H), 3.44 (m, 2H), 2.60 (m, 2H);

3-[1-methyl-4[1-methyl-4[1-methyl-4[5(α-bromoacrylamido)indole-2-carboxamido]pyrrole-2-carboxamido]pyrrole-2-carboxamido]pyrrole-2-carboxamido]propionamidine hydrochloride;
FAB-MS: m/z 744, (100, [M+H]$^+$)
U.V. (EtOH 95%) $\lambda_{max}$=500, $\epsilon$=39053
PMR (DMSO-d$_6$) δ: 11.70 (d, J=1.7 Hz, 1H), 10.42 (s, 1H), 10.15 (s, 1H), 9.99 (s, 1H), 9.90 (s, 1H), 8.98 (b.s. , 2H), 8.67 (b.s. , 2H), 8.20 (t, J=5.7 Hz, 1H), 7.95 (d, J=2.1 Hz, 1H), 7.36 (m, 2H), 7.26 (d, J=1.8 Hz, 1H), 7.24 (s, 1H), 7.22 (d, J=1.8 Hz, 1H), 7.16 (d, J=1.8 Hz, 1H) 7.06 (d, J=1.8 Hz, 1H), 7.03 (d, J=1.8 Hz, 1H), 6.91 (d, J=1.8 Hz, 1H), 6.72 (d, J=3.0 Hz, 1H), 6.23 (d, J=3.0 Hz, 1H), 3.84 (s, 3H), 3.80 (s, 3H), 3.77 (s, 3H), 3.46 (m, 2H), 2.59 (m, 2H);

3-[1-methyl-4[1-methyl-4[1-methyl-4[1-methyl-5(α-bromoacrylamido)indole-2-carboxamido]pyrrole-2-carboxamido]pyrrole-2-carboxamido]pyrrole-2-carboxamido]propionamidine hydrochloride;
FAB-MS: m/z 760, (100, [M+H]$^+$)
PMR (DMSO-d$_6$) δ: 10.44 (s, 1H), 10.23 (s, 1H), 10.00 (s, 1H), 9.93 (s, 1H), 8.97 (b.s., 2H), 8.60 (b.s., 2H), 8 .22 (t, J=5.7 Hz, 1H), 8.05 (d, J=1.8 Hz, 1H), 7.54 (d, J=8.9 Hz, 1H), 7.47 (dd, J=8.9 Hz and J=1.9 Hz, 1H), 7.25 (d, J=1.8 Hz, 1H), 7.21 (s, 1H), 7.19 (d, J=1.8 Hz, 1H), 7.12 (d, J=1.8 Hz, 1H), 7.07 (d, J=1.8 Hz, 1H), 7.05 (d, J=1.8 Hz, 1H), 6.95 (d, J=1.8 Hz, 1H), 6.77 (d, J=3.1 Hz, 1H), 6.29 (d, J=3.1 Hz, 1H), 4.01 (s, 3H), 3.88 (s, 3H), 3.85 (s, 3H), 3.81 (s, 3H), 3.50 (m, 2H), 2.61 (m, 2H)

3-[1-methyl-4[1-methyl-4[1-methyl-4[5(α-bromoacrylamido)benzothiophene-2-carboxamido]pyrrole-2-carboxamido]pyrrole-2-carboxamido]pyrrole-2-carboxamido]propionamidine hydrochloride;
FAB-MS: m/z 760, (20, [M+H]$^+$)
PMR (DMSO-d$_6$) δ: 10.71 (s, 1H), 10.48 (s, 1H), 9.99 (s, 1H), 9.90 (s, 1H), 8.96 (b.s., 2H), 8.65 (b.s., 2H), 8.32 (d, J=2.1 Hz, 1H), 8.24 (s, 1H), 8.19 (t, J=5.6 Hz, 1H), 7.95 (d, J=9.0 Hz, 1H), 7.65 (dd, J=2.1 Hz and J=9.0 Hz, 1H), 7.29 (d, J=1.8 Hz, 1H), 7.22 (d, J=1.8 Hz, 1H), 7.16 (d, J=1.8 Hz, 1H), 7.09 (d, J=1.8 Hz, 1H), 7.03 (d, J=1.8 Hz, 1H), 6.91 (d, J=1.8 Hz, 1H), 6.80 (d, J=3.0 Hz, 1H), 6.31 (d, J=3.0 Hz, 1H), 3.84 (s, 3H), 3.80 (s, 3H), 3.77 (s, 3H), 3.46 (m, 2H), 2.58 (m, 2H);

3-[1-methyl-4[1-methyl-4[1-methyl-4[5(α-bromoacrylamido)benzothiazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5(α-bromoacrylamido)benzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[1-methyl-5(α-bromoacrylamido)benzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5(α-chloroacrylamido)indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[1-methyl-5(α-chloroacrylamido)indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5(α-chloroacrylamido)benzoimidazole-2-carboxamido]pyrrole-2-carboxamido)pyrrole-2-carboxamido]pyrrole-2-carboxamido]propionamidine hydrochloride.

EXAMPLE 3

3-[1-methyl-4[1-methyl-4[1-methyl-4[1-methyl-5-[4-N,N-bis(2-chloroethyl)aminobenzene-1-carboxamido]indole-2-carboxamido]pyrrole-2-carboxamido]pyrrole-2-carboxamido]pyrrole-2-carboxamido]propionamidine hydrochloride Step I: The intermediate 1-methyl-5-[4-N,N-bis(2-chloroethyl)aminobenzene-1-carboxamido]indole-2-carboxylic acid To a solution of 495 mg of 4-N,N-bis(2-chloroethyl) aminobenzoic acid (prepared as reported in Example 1, Step I) in 20 ml of benzene, 1 ml of thionyl chloride was added. The mixture was refluxed for two hours, the solvent evaporated under vacuum, the crude solid residue dissolved in 15 ml of dioxane and added portionwise to a solution of 167 mg of 1-methyl-5-aminoindole-2-carboxylic acid (prepared as reported in J.Am.Chem.Soc. 80, 4621 (1958)) and 239 mg of sodium bicarbonate in 20 ml of water.

The mixture was stirred for one hour and then added with 2N hydrochloric acid up to pH=4. The solvent was evaporated in vacuo and the residue purified by flash chromatography on silica gel with a methylene chloride/methanol mixture, yielding 400 mg of the intermediate.

By analogous procedure and using the opportune starting materials the following products can be obtained:

5-[4-N,N-bis(2-chloroethyl)aminobenzene -1-carboxamido] indole-2-carboxylic acid;

5-[4-N,N-bis(2-chloroethyl)aminobenzene -1-carboxamido] benzofurane-2-carboxylic acid;

5-[4-N,N-bis(2-chloroethyl)aminobenzene -1-carboxamido] benzothiophene-2-carboxylic acid;

5-[4-N,N-bis(2-chloroethyl)aminobenzene -1-carboxamido] benzoimidazole-2-carboxylic acid;

1-methyl-5-[4-N,N-bis(2-chloroethyl)aminobenzene -1-carboxamido]benzoimidazole-2-carboxylic acid;

5-[4-N,N-bis(2-chloroethyl)aminobenzene -1-carboxamido] benzothiazole-2-carboxylic acid;

5-[4-N,N-bis(2-bromoethyl)aminobenzene -1-carboxamido] indole-2-carboxylic acid;

1-methyl-5-[4-N,N-bis(2-bromoethyl)aminobenzene -1-carboxamido]indole-2-carboxylic acid;

5-[4-N,N-bis(2-bromoethyl)aminobenzene -1-carboxamido] benzoimidazole-2-carboxylic acid;

5-[4-[N-ethyl-N-(2-chloroethyl)]aminobenzene -1-carboxamido]indole-2-carboxylic acid;

1-methyl-5-[4-N,N-bis(2-chloroethyl)aminobenzene -1-carboxamido]indole-2-carboxylic acid;

5-[4-N,N-bis(2-chloroethyl)aminobenzene -1-carboxamido] benzoimidazole-2-carboxylic acid;

1-methyl-5-[4-N,N-bis(2-chloroethyl)aminobenzene -1-carboxamido]benzoimidazole-2-carboxylic acid.

Step II: The Title Compound

To a solution of 320 mg of intermediate (prepared as reported in Step I) in 10 ml of benzene, 0.5 ml of thionyl chloride were added. The mixture was refluxed for two hours, the solvent evaporated under vacuum, the crude solid residue dissolved in 15 ml of dioxane and added portionwise to a solution of 200 mg of N-deformyldistamycin A dihydrochloride (prepared as reported in J.Med.Chem. 32, 774–778 (1989)), 95 mg of sodium bicarbonate in 10 ml of water.

The mixture was stirred for one hour and then added of 2N hydrochloric acid up to pH=4. The solvent was evaporated in vacuo and the residue purified by flash chromatography (methylene chloride/methanol:8/2) to yield 250 mg of the title compound as a pale yellow solid.

FAB-MS: m/z 869, (40, [M+H]$^+$)

PMR (DMSO-d$_6$) δ: 10.39 (s, 1H), 9.98 (s, 1H), 9.91 (s, 1H), 9.88 (s, 1H) 8.97 (b.s., 2H), 8.63 (b.s., 2H), 8.20 (t, J=5.6 Hz, 1H), 8.15 (d, J=1.8 Hz, 1H), 7.90 (m, 2H), 7.58 (dd, J=9.0 Hz and J=1.8 Hz , 1H), 7.50 (d, J=9.0 Hz, 1H), 7.33 (d, J=1.8 Hz, 1H), 7.24 (d, J=1.8 Hz, 1H), 7.21 (s, 1H), 7.19 (d, J=1.8 Hz, 1H), 7.18 (d, J=1.8 Hz, 1H), 7.12 (d, J=1.8 Hz, 1H), 7.07 (d, J=1.8 Hz, 1H), 6.95 (d, J=1.8 Hz, 1H), 6.84 (m, 2H), 4.01 (s, 3H), 3.88 (s, 3H), 3.84 (s, 3H), 3.80 (s, 3H), 3.78 (m, 8H), 3.50 (m, 2H), 2.61 (m, 2H).

By analogous procedure and using the opportune starting materials the following products can be obtained:

3-[1-methyl-4[1-methyl-4[5-[4-N,N-bis(2-chloroethyl) aminobenzene-1-carboxamido]indole-2-carboxamido] pyrrole-2-carboxamido]pyrrole-2-carboxamido) propionamidine hydrochloride; 3-[1-methyl-4[1-methyl-4[5-[4-N,N-bis(2-chloroethyl)aminobenzene-1-carboxamido]benzoimidazole-2-carboxamido]pyrrole-2-carboxamido]pyrrole-2-carboxamido]propionamidine hydrochloride;

3-[1-methyl-4[1-methyl-4[1-methyl-4[5-[4-N,N-bis(2-chloroethyl aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N,N-bis(2-chloroethyl)aminobenzene-1-carboxamido] benzothiophene-2-carboxamido]pyrrole-2-carboxamido] pyrrole-2-carboxamido]pyrrole-2-carboxamido] propionamidine hydrochloride;

FAB-MS: m/z 871, (20, [M+H]$^+$)

U.V. (EtOH 95%) λ$_{max}$=313.8, ε=48830

PMR (DMSO-d$_6$) δ: 10.70 (s, 1H), 10.11 (s, 1H), 9.99 (s, 1H), 9.90 (s, 1H), 9.0 (b.s., 2H), 8.7 (b.s., 2H), 8.45 (d, J=1.7 Hz, 1H), 8.24 (s, 1H), 8.20 (t, J=5.7 Hz, 1H), 7.90 (m, 3H), 7.76 (dd, J=9.0 Hz and J=2.1 Hz, 1H), 7.30 (d, J=1.7 Hz, 1H), 7.22 (d, J=1.7 Hz, 1H), 7.16 (d, J=1.7 Hz, 1H), 7.10 (d, J=1.7 Hz, 1H), 7.03 (d, J=1.7 Hz, 1H), 6.90 (d, J=1.7 Hz, 1H), 6.82 (m, 2H), 3.84 (s, 3H), 3.81 (s, 3H), 3.77 (s, 3H), 3.6–3.9 (m, 8H), 3.46 (m, 2H), 2.60 (m, 2H);

3-[1-methyl-4[1-methyl-4[1-methyl-4[5-[4-N,N-bis(2-chloroethyl)aminobenzene-1-carboxamido]benzofurane-2-carboxamido]pyrrole-2-carboxamido]pyrrole-2-carboxamido]pyrrole-2-carboxamido]propionamidine hydrochloride;

FAB-MS: m/z 855, (8, [M+H]$^+$)

U.V. (EtOH 95%) λ$_{max}$=313, ε=63866

PMR (DMSO-d$_6$) δ: 10.72 (s, 1H), 10.08 (s, 1H), 10.04 (s, 1H), 9.93 (s, 1H), 8.90 (b.s., 4H), 8.28 (d, J=2.6 Hz, 1H), 8.23 (t, J=5.6 Hz, 1H), 7.91 (m, 2H), 7.76 (dd, J=9.0 Hz and J=2.1 Hz, 1H), 7.68 (s, 1H), 7.65 (d, J=9.0 Hz, 1H), 7.34 (d, J=1.7 Hz, 1H), 7.26 (d, J=1.7 Hz, 1H), 7.19 (d, J=1.7 Hz, 1H), 7.16 (d, J=1.7 Hz, 1H), 7.07 (d, J=1.7 Hz, 1H), 6.95 (d, J=1.7 Hz, 1H), 6.86 (m, 2H), 3.88 (s, 3H), 3.85 (s, 3H), 3.81 (s, 3H), 3.7–3.9 (m, 8H), 3.50 (m, 2H), 2.62 (m, 2H).

3-[1-methyl-4[1-methyl-4[1-methyl-4[5-[4 -N,N-bis(2-chloroethyl)aminobenzene-1-carboxamido] benzoimidazole-2-carboxamido]pyrrole-2-carboxamido] pyrrole-2-carboxamido]pyrrole-2-carboxamido] propionamidine hydrochloride;

FAB-MS: m/z 856, (100, [M+H]$^+$)

PMR (DMSO-d$_6$) δ: 11.05 (s, 1H), 10.06 (s, 1H), 10.04 (s, 1H), 9.92 (s, 1H), 8.96 (b.s., 2H), 8.60 (b.s., 2H), 8.28 (m,

1H), 8.22 (t, J=5.9 Hz, 1H), 7.90 (m, 2H), 7.64 (m, 2H), 7.39 (d, J=1.7 Hz, 1H), 7.25 (d, J=1.7 Hz, 1H), 7.20 (d, J=1.7 Hz, 1H), 7.18 (d, J=1.7 Hz, 1H), 7.07 (d, J=1.7 Hz, 1H), 6.95 (d, J=1.7 Hz, 1H), 6.85 (m, 2H), 3.6–3.9 (m, 17H), 3.50 (m, 2H), 3.60 (m, 2H);

3-[1-methyl-4[1-methyl-4[1-methyl-4[1-methyl-5-[4-N,N-bis(2-chloroethyl)aminobenzene-1-carboxamido]benzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N,N-bis(2-chloroethyl)aminobenzene-1-carboxamido]benzothiazole-2-carboxamido]pyrrole-2-carboxamido]pyrrole-2-carboxamido]pyrrole-2-carboxamido]propionamidine hydrochloride;

3-[1-methyl-4[1-methyl-4[5-[4-N,N-bis(2-bromoethyl)aminobenzene-1-carboxamido]indole-2-carboxamido]pyrrole-2-carboxamido]pyrrole-2-carboxamido]propionamidine hydrochloride;

3-[1-methyl-4[1-methyl-4[1-methyl-5-[4-N,N-bis(2-bromoethyl)aminobenzene-1-carboxamido]indole-2-carboxamido]pyrrole -2-carboxamido]pyrrole-2-carboxamido]propionamidine hydrochloride;

3-[1-methyl-4[1-methyl-4[5-[4-N,N-bis(2-bromoethyl)aminobenzene-1-carboxamido]benzoimidazole-2-carboxamido]pyrrole-2-carboxamido]pyrrole-2-carboxamido]propionamidine hydrochloride;

3-[1-methyl-4[1-methyl-4[1-methyl-4[5-[4-N,N-bis(2-bromoethyl)aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[1-methyl-5-[4-N,N-bis(2-bromoethyl)aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N,N-bis(2-bromoethyl)aminobenzene-1-carboxamido]benzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N-ethyl-N(2-chloroethyl)aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N-ethyl-N(2-chloroethyl)aminobenzene-1-carboxamido]benzoimidazole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[1-methyl-5-[4-N-ethyl-N(2-chloroethyl)aminobenzene-1-carboxamido]indole-2-carboxamido]pyrrole-2-carboxamido]pyrrole-2-carboxamido]propionamidine hydrochloride;

3-[1-methyl-4[1-methyl-4[1-methyl-4[1-methyl-5-[4-N-ethyl-N(2-chloroethyl)aminobenzene-1-carboxamido]benzoimidazole-2-carboxamido]pyrrole-2-carboxamido]pyrrole-2-carboxamido]pyrrole-2-carboxamido]propionamidine hydrochloride.

EXAMPLE 4

3-[1-methyl-4[1-methyl-4[1-methyl-4[5-[4-N,N-bis(2-chloroethyl)aminobenzene-1-carboxamido]benzothiophene-2-carboxamido]pyrrole-2-carboxamido]pyrrole-2-carboxamido]pyrrole-2-carboxamido]propionamidine hydrochloride Step I: The intermediate 3-[1-methyl-4-[1-methyl-4[1-methyl-4[4-nitrobenzothiophene-2-carboxamido]pyrrole-2-carboxamido]pyrrole-2-carboxamido]pyrrole-2-carboxamido]propionamidine dihydrochloride To a solution of 156 mg of 4-nitrobenzothiophene-2-carboxylic acid (prepared as reported in Synth.Commun. 21, 959 (1991)) in 10 ml of benzene, 0.5 ml of thionyl chloride were added. The mixture was refluxed for two hours, the solvent evaporated under vacuum, the crude solid residue dissolved in 15 ml of dioxane and added portionwise to a solution of 200 mg of N-deformyldistamycin A dihydrochloride (prepared as reported in J.Med.Chem. 32,774–778 (1989)), 95 mg of sodium bicarbonate in 10 ml of water.

The mixture was stirred for one hour and then added of 2N hydrochloric acid up to pH=4. The solvent was evaporated in vacuo and the residue purified by flash chromatography with a methylene chloride/methanol mixture to yield 220 mg of the title compound as a solid.

By analogous procedure and using the opportune starting materials the following products can be obtained:

3-[1-methyl-4[1-methyl-4[1-methyl-4[4-nitrobenzofurane-2-carboxamido]pyrrole-2-carboxamido]pyrrole-2-carboxamido]pyrrole-2-carboxamido]propionamidine dihydrochloride;

3-[1-methyl-4[1-methyl-4[1-methyl-4[4-nitroindole-2-carboxamido]pyrrole-2-carboxamido]pyrrole-2-carboxamido]pyrrole-2-carboxamido]propionamidine dihydrochloride;

3-[1-methyl-4[1-methyl-4[4-nitroindole-2-carboxamido]pyrrole-2-carboxamido]pyrrole-2-carboxamido]propionamidine dihydrochloride;

3-[1-methyl-4[1-methyl-4[1-methyl-4[1-methyl-4-nitroindole-2-carboxamido]pyrrole-2-carboxamido]pyrrole-2-carboxamido]pyrrole-2-carboxamido]propionamidine dihydrochloride;

3-[1-methyl-4[1-methyl-4[1-methyl-4-nitroindole-2-carboxamido]pyrrole-2-carboxamido]pyrrole-2-carboxamido]propionamidine dihydrochloride;

3-[1-methyl-4[1-methyl-4[1-methyl-4[4-nitrobenzoimidazole-2-carboxamido]pyrrole-2-carboxamido]pyrrole-2-carboxamido]pyrrole-2-carboxamido]propionamidine dihydrochloride;

3-[1-methyl-4[1-methyl-4[4-nitrobenzoimidazole-2-carboxamido]pyrrole-2-carboxamido]pyrrole-2-carboxamido]propionamidine dihydrochloride;

3-[1-methyl-4[1-methyl-4[1-methyl-4[1-methyl-4-nitrobenzoimidazole-2-carboxamido]pyrrole-2-carboxamido]pyrrole-2-carboxamido]pyrrole-2-carboxamido]propionamidine dihydrochloride;

3-[1-methyl-4[1-methyl-4[1-methyl-4[4-nitrobenzothiazole-2-carboxamido]pyrrole-2-carboxamido]pyrrole-2-carboxamido]pyrrole-2-carboxamido]propionamidine dihydrochloride.

Step II: The Title Compound

The derivative (220 mg) obtained from Step I was dissolved in 10 ml of DMF and reduced over Pd catalyst (10% on charcoal) under reduced pressure (50 psi) in a Parr apparatus. The solution obtained after filtration of the catalyst was evaporated in vacuo and the solid residue dissolved in 5 ml of dry DMF, cooled to 5° C. and added with 0.055 ml of N,N'-diisopropylethylamine. After 10 min, 100 mg of 4-N,N-bis(2-chloroethyl)aminobenzoic acid (prepared as reported in Example 1, Step I) and 123 mg of N-ethyl-N'-(3-dimethylaminopropyl)carbodiimide were added. The solution was stirred for 12 hours at room temperature, then 2N hydrochloric acid was added up to pH=4. The solvent was evaporated and the crude residue purified by flash chromatography (methylene chloride/methanol:8/2) to give 200 mg of the title compound as a yellow solid.

FAB-MS: m/z 871, (20, [M+H]$^+$)

U.V. (EtOH 95%) $\lambda_{max}$=313.8, $\epsilon$=48830

PMR (DMSO-d$_6$) δ: 10.70 (s, 1H), 10.11 (s, 1H), 9.99 (s, 1H), 9.90 (s, 1H), 9.0 (b.s., 2H), 8.7 (b.s., 2H), 8.45 (d, J=1.7 Hz, 1H), 8.24 (s, 1H), 8.20 (t, J=5.7 Hz, 1H), 7.90 (m, 3H), 7.76 (dd, J=9.0 Hz and J=2.1 Hz, 1H), 7.30 (d, J=1.7 Hz, 1H), 7.22 (d, J=1.7 Hz, 1H), 7.16 (d, J=1.7 Hz, 1H), 7.10 (d, J=1.7 Hz, 1H), 7.03 (d, J=1.7 Hz, 1H), 6.90 (d, J=1.7 Hz, 1H), 6.82 (m, 2H), 3.84 (s, 3H), 3.81 (s, 3H), 3.77 (s, 3H), 3.6–3.9 (m, 8H), 3.46 (m, 2H), 2.60 (m, 2H).

By analogous procedure and using the opportune starting materials the following products can be obtained:

3-[1-methyl-4[1-methyl-4[1-methyl-4[5(α-bromoacrylamido)indole-2-carboxamido]pyrrole-2-carboxamido]pyrrole-2-carboxamido]propionamidine hydrochloride;

FAB-MS: m/z 269, (10, [M+H]$^+$)

U.V. (EtOH 95%) $\lambda_{max}$=310 , $\epsilon$=35011

PMR (DMSO-d$_6$) δ: 10.39 (s, 1H), 10.18 (s, 1H), 9.93 (s, 1H), 8.92 (b.s., 2H), 8.54 (b.s., 2H), 8.19 (t, J=5.7 Hz, 1H), 8.01 (d, J=1.5 Hz, 1H), 7.50 (d, J=9.0 Hz, 1H), 7.42 (dd, J=9.0 Hz and J=1.5 Hz, 1H), 7.29 (d, J=1.8 Hz, 1H), 7.16 (s, 1H), 7.15 (d, J=1.8 Hz, 1H) 7.06 (d, J=1.8 Hz, 1H), 6.92 (d, J=1.8 Hz, 1H), 6.72 (d, J=3.1 Hz, 1H), 6.25 (d, J=3.1 Hz, 1H), 3.97 (s, 3H), 3.83 (s, 3H), 3.77 (s, 3H), 3.44 (m, 2H), 2.60 (m, 2H);

3-[1-methyl-4[1-methyl-4[1-methyl-4[5(α-bromoacrylamido)benzofurane-2-carboxamido]pyrrole-2-carboxamido]pyrrole-2-carboxamido]pyrrole-2-carboxamido]propionamidine hydrochloride;

FAB-MS: m/z 746, (25, [M+H]$^+$)

U.V. (EtOH 95%) $\lambda_{max}$=315.4, $\epsilon$=42622

PMR (DMSO-d$_6$) δ: 10.69 (s, 1H), 10.39 (s, 1H), 10.00 (s, 1H), 9.90 (s, 1H), 8.92 (b.s., 2H), 8.52 (b.s., 2H), 8.2 (m, 2H), 7.66 (m, 3h), 7.32 (d, J=1.8 Hz, 1H), 7.24 (d, J=1.8 Hz, 1H), 7.17 (d, J=1.8 Hz, 1H), 7.15 (d, J=1.8 Hz, 1H) 7.07 (d, J=1.8 Hz, 1H), 6.96 (d, J=1.8 Hz, 1H), 6.77 (d, J=3.1 Hz, 1H), 6.31 (d, J=3.1 Hz, 1H), 3.87 (s, 3H), 3.84 (s, 3H), 3.80 (s, 3H), 3.51 (m, 2H), 2.60 (m, 2H);

3-[1-methyl-4[1-methyl-4[1-methyl-4[5(α-chloroacrylamido)benzoimidazole-2-carboxamido]pyrrole-2-carboxamido]pyrrole-2-carboxamido]pyrrole-2-carboxamido]propionamidine hydrochloride 3-[1-methyl-4[1-methyl-4[5-[4-N,N-bis(2-chloroethyl)aminobenzene-1-carboxamido]indole-2-carboxamido]pyrrole-2-carboxamido]pyrrole-2-carboxamiido]propionamidine hydrochloride;

3-[1-methyl-4[1-methyl-4[5-[4-N,N-bis(2-chloroethyl)aminobenzene-1-carboxamido]benzoimidazole-2-carboxamido]pyrrole-2-carboxamido]pyrrole-2-carboxamido]propionamidine hydrochloride;

3-[1-methyl-4[1-methyl-4[1-methyl-4[5-[4N-ethyl-n(2-chloroethyl)aminobenzene-1-carboxamido]indole-2-carboxamido]pyrrole-2-carboxamido]pyrrole-2-carboxamido]pyrrole-2-carboxamido]propionamidine hydrochloride;

3-[1-methyl-4[1-methyl-4[1-methyl-4[5-[4-N-ethyl-n(2-chloroethyl)aminobenzene-1-carboxamido]benzoimidazole-2-carboxamido]pyrrole-2-carboxamido]pyrrole-2-carboxamido]pyrrole-2-carboxamido]propionamidine hydrochloride.

What is claimed is:

1. A compound which is a benzoheterocyclic distamycin derivative of formula:

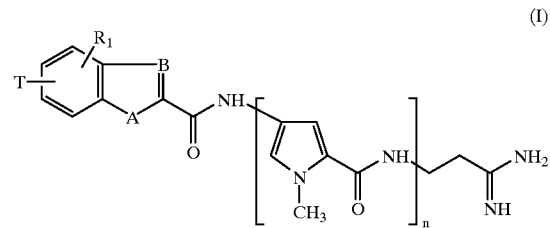

(I)

wherein:

n is 2, 3 or 4;

A is NR, wherein R is hydrogen or $C_1$–$C_4$ alkyl;

B is CH;

$R_1$ is hydrogen or $C_1$–$C_4$ alkyl;

T is selected from:

(i)

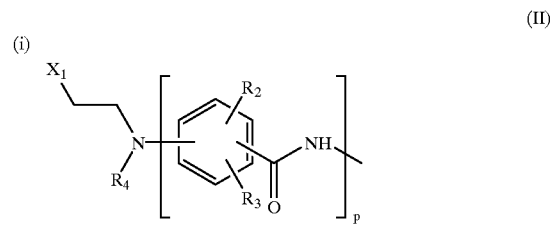

(II)

wherein:

p is zero or 1; $R_2$ and $R_3$ are selected, each independently, from: hydrogen, $C_1$–$C_4$ alkyl optionally substituted by one or more fluorine atoms, and $C_1$–$C_4$ alkoxy; $R_4$ is $C_1$–$C_4$ alkyl or $C_1$–$C_3$ haloalkyl; $X_1$ is a halogen atom; and (ii)

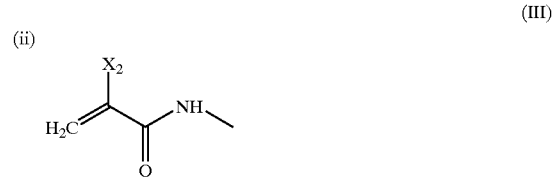

(III)

wherein $X_2$ is a halogen atom;

or a pharmaceutically acceptable salt thereof.

2. A compound according to claim 1, wherein:

n is 2 or 3;

A is NH or NCH$_3$;

B is CH;

$R_1$ is hydrogen;

T is a group of formula (II) according to item (i), wherein $X_1$ is chlorine or bromine; $R_4$ is ethyl, 2-chloroethyl or 2-bromoethyl; $R_2$ and $R_3$ are, each independently, hydrogen or methyl; p is zero or 1; or T is a group of formula (III) according to item (ii), wherein $X_2$ is bromine or chlorine.

3. A compound according to claim 1, selected from:

3-[1-methyl-4[1-methyl-4[1-methyl-4[5-N,N-bis(2-chloroethyl)aminoindole-2-carboxamido]pyrrole-2-carboxamido]pyrrole-2-carboxamido]pyrrole-2-carboxamido]propionamidine;

3-[1-methyl-4[1-methyl-4[1-methyl-4[1-methyl-5-N,N-bis(2-chloroethyl)aminoindole-2-carboxamido]pyrrole-2-carboxamido]pyrrole-2-carboxamido]pyrrole-2-carboxamido]propionamidine;

3-[1-methyl-4[1-methyl-4[1-methyl-4[5-N,N-bis(2-bromoethyl)aminoindole-2-carboxamido]pyrrole-2-carboxamido]pyrrole-2-carboxamido]pyrrole-2-carboxamido]propionamidine;

3-[1-methyl-4[1-methyl-4[1-methyl-4[5($\alpha$-bromoacrylamido)indole-2-carboxamido]pyrrole-2-carboxamido]pyrrole-2-carboxamido]propionamidine;

3-[1-methyl-4[1-methyl-4[1-methyl-4[5($\alpha$-bromoacrylamido)indole-2-carboxamido]pyrrole-2-carboxamido]pyrrole-2-carboxamido]pyrrole-2-carboxamido]propionamidine;

3-[1-methyl-4[1-methyl-4[1-methyl-4[1-methyl-5($\alpha$-bromoacrylamido)indole-2-carboxamido]pyrrole-2-carboxamido]pyrrole-2-carboxamido]pyrrole-2-carboxamido]propionamidine;

3-[1-methyl-4[1-methyl-4[1-methyl-4[5($\alpha$-chloroacrylamido)indole-2-carboxamido]pyrrole-2-carboxamido]pyrrole-2-carboxamido]pyrrole-2-carboxamido]propionamidine;

3-[1-methyl-4[1-methyl-4[1-methyl-4[1-methyl-5($\alpha$-chloroacrylamido)indole-2-carboxamido]pyrrole-2-carboxamido]pyrrole-2-carboxamido]pyrrole-2-carboxamido]propionamidine;

3-[1-methyl-4[1-methyl-4[1-methyl-4[5-[4-N,N-bis(2-chloroethyl)aminobenzene-1-carboxamido]indole-2-carboxamido]pyrrole-2-carboxamido]pyrrole-2-carboxamido]pyrrole-2-carboxamido]propionamidine;

3-[1-methyl-4[1-methyl-4[1-methyl-4[1-methyl-5-[4-N,N-bis(2-chloroethyl)aminobenzene-1-carboxamido]indole-2-carboxamido]pyrrole-2-carboxamido]pyrrole-2-carboxamido]pyrrole-2-carboxamido]propionamidine;

3-[1-methyl-4[1-methyl-4[5-[4 -N,N-bis(2-bromoethyl)aminobenzene-1-carboxamido]indole-2-carboxamido]pyrrole-2-carboxamido]pyrrole-2-carboxamido]propionamidine;

3-[1-methyl-4[1-methyl-4[1-methyl-5-[4-N,N-bis(2-bromoethyl)aminobenzene-1-carboxamido]indole-2-carboxamido]pyrrole-2-carboxamido]pyrrole-2-carboxamido]propionamidine;

3-[1-methyl-4[1-methyl-4[1-methyl-4[5-[4-N,N-bis(2-bromoethyl)aminobenzene-1-carboxamido]indole-2-carboxamido]pyrrole-2-carboxamido]pyrrole-2-carboxamido]pyrrole-2-carboxamido]propionamidine;

3-[1-methyl-4[1-methyl-4[1-methyl-4[1-methyl-5-[4-N,N-bis(2-bromoethyl)aminobenzene-1-carboxamido]indole-2-carboxamido]pyrrole-2-carboxamido]pyrrole-2-carboxamido]pyrrole-2-carboxamido]propionamidine;

3-1-methyl-4[1-methyl-4[1-methyl-4[5-[4-N-ethyl-N(2-chloroethyl)aminobenzene-1-carboxamido]indole-2-carboxamido]pyrrole-2-carboxamido]pyrrole-2-carboxamido]propionamidine;

3-[1-methyl-4[1-methyl-4[1-methyl-4[1-methyl-5-[4-N-ethyl-N(2-chloroethyl)aminobenzene-1-carboxamido]indole-2-carboxamido]pyrrole-2-carboxamido]pyrrole-2-carboxamido]pyrrole-2-carboxamido]propionamidine;

and the pharmaceutically acceptable salts thereof.

4. A pharmaceutical composition which comprises an effective amount of a compound as defined in claim 1 as an active principle, in association with one or more pharmaceutically acceptable carriers and/or diluents.

5. A method of inhibiting growth of a tumor or tumors in a mammal by administering a compound of formula (I) of claim 1 to the mammal.

6. The method of claim 5 wherein said tumor or tumors is a carcinoma.

7. The method of claim 6 wherein said carcinoma is selected from mammary carcinoma, lung carcinoma, bladder carcinoma, colon carcinoma.

8. The method of claim 5 wherein the mammal is a human.

9. A method of treating a viral infection by administering a compound of formula (I) of claim 1.

10. A process for producing a compound as defined in claim 1, which process comprises:

(1)(a) reacting a compound of formula:

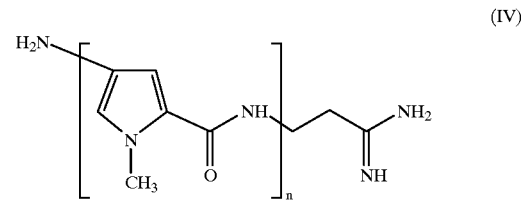

(IV)

wherein n is 2, 3 or 4, with a compound of formula:

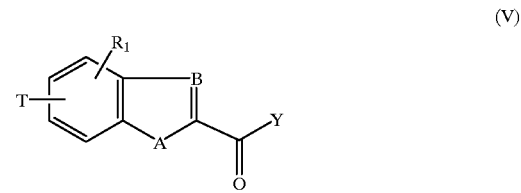

(V)

wherein:
A is NR, wherein R is hydrogen or $C_1$–$C_4$ alkyl;
B is CH;
$R_1$ is hydrogen or $C_1$–$C_4$ alkyl;
T is selected from:

(i)

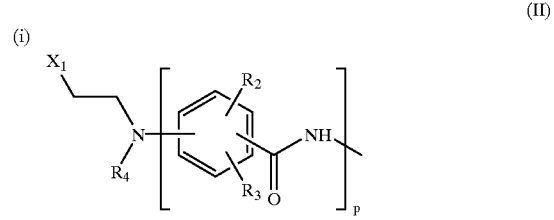

(II)

wherein:
p is zero or 1; $R_2$ and $R_3$ are selected, each independently, from: hydrogen, $C_1$–$C_4$ alkyl optionally substituted by one or more fluorine atoms, and $C_1$–$C_4$ alkoxy; $R_4$ is $C_1$–$C_4$ alkyl or $C_1$–$C_3$ haloalkyl;

$X_1$ is a halogen atom; and (ii)

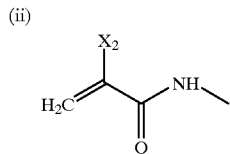
(III)

wherein $X_2$ is a halogen atom;

Y is hydroxy or a leaving group;

to obtain a compound of formula (I) as defined above; or:

(b) reacting a compound of formula:

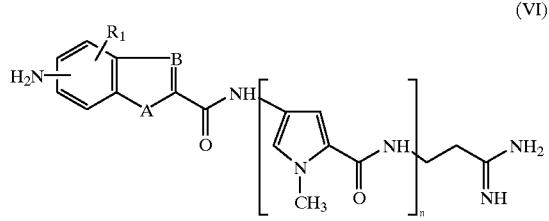
(VI)

wherein n, A, B, and $R_1$ are defined as above, with a compound of formula:

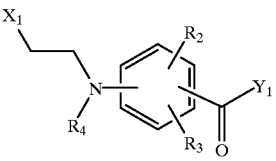
(VIIa)

wherein $X_1$, $R_2$, $R_3$, and $R_4$ are defined as above, and $Y_1$ is hydroxy or a leaving group;

or with a compound of formula:

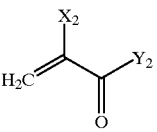
(VIIb)

wherein $X_2$ is as defined above, and $Y_2$ is hydroxy or a leaving group;

to obtain a compound of formula (I) as defined above, wherein T is a group of formula (II) according to item (i) with p equal to 1, or a group of formula (III) according to item (ii); or:

(c) reacting a compound of formula:

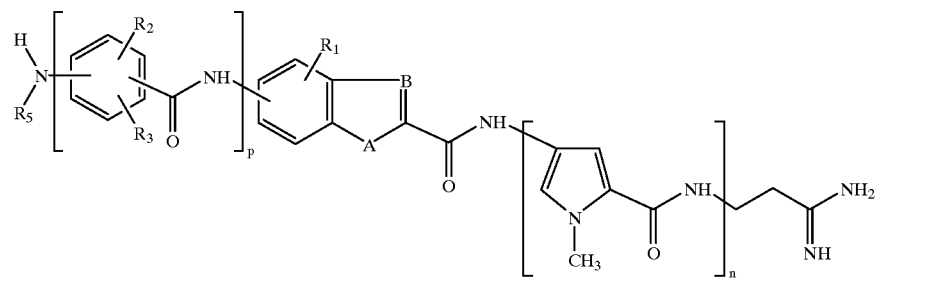
(VIII)

wherein p, n, A, B, $R_1$, $R_2$, and $R_3$ are defined as above, and $R_5$ is hydrogen or $C_1$–$C_4$ alkyl, with ethylene oxide, so obtaining a compound of formula:

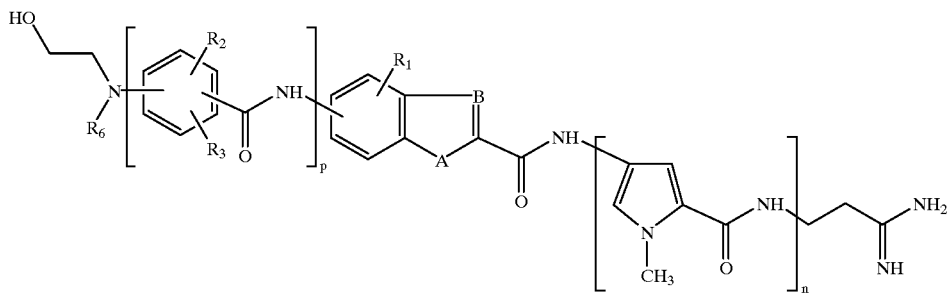

(IX)

wherein p, n, A, B, $R_1$, $R_2$, and $R_3$ are defined as above, and $R_6$ is equal to $R_5$ when $R_5$ is $C_1$–$C_4$ alkyl, or $R_6$ is equal to —$CH_2CH_2$—OH when $R_5$ is hydrogen;

and then reacting the compound of formula (IX) with a halogenating agent, to obtain a compound of formula (I) as defined above, wherein T is a group of formula (II) according to item (i) with p equal to zero or 1; and (2) if necessary, converting the so obtained compound of formula (I) into a pharmaceutically acceptable salt thereof.

* * * * *